United States Patent [19]

Holme

[11] Patent Number: 5,783,093
[45] Date of Patent: Jul. 21, 1998

[54] BLOOD CELL CONCENTRATES USING A SINGLE SOLUTION FOR ANTICOAGULATION AND PRESERVATION

[75] Inventor: Stein Holme, Tucson, Ariz.

[73] Assignee: Haemonetics Corporation, Braintree, Mass.

[21] Appl. No.: 778,033

[22] Filed: Jan. 2, 1997

[51] Int. Cl.⁶ .......................... A61K 35/14; A61K 35/18; A61M 1/36

[52] U.S. Cl. .......................... 210/767; 210/806; 435/2; 604/4

[58] Field of Search .......................... 210/645, 782, 210/787, 749, 789, 806, 767; 604/4, 5, 6; 435/2

[56] References Cited

U.S. PATENT DOCUMENTS

| | | | |
|---|---|---|---|
| 4,223,672 | 9/1980 | Terman et al. | 210/782 |
| 4,356,172 | 10/1982 | Nakao et al. | 435/2 |
| 4,855,063 | 8/1989 | Carmen et al. | 210/749 |
| 4,961,828 | 10/1990 | Holme et al. | 435/2 |
| 5,135,667 | 8/1992 | Schoendorfer | 210/782 |
| 5,387,187 | 2/1995 | Fell et al. | 210/782 |
| 5,494,590 | 2/1996 | Smith et al. | 435/2 |
| 5,523,004 | 6/1996 | Tanokura et al. | 210/782 |
| 5,614,106 | 3/1997 | Payrat et al. | 210/767 |

*Primary Examiner*—John Kim
*Attorney, Agent, or Firm*—Cesari and McKenna, LLP

[57] ABSTRACT

A method for preparing red blood cell concentrates uses a single additive solution composition having a reduced citrate concentration both for anticoagulation of whole blood and for preserving red blood cells in storage.

28 Claims, 6 Drawing Sheets

BLOOD CELL CONCENTRATES USING A SINGLE SOLUTION FOR ANTICOAGULATION AND PRESERVATION

FIELD OF THE INVENTION

This invention relates to collection and preservation of blood products. Particularly, this invention relates to methods and compositions for preparation of red blood cell concentrates from collected whole blood.

BACKGROUND OF THE INVENTION

The progressive loss of red blood cell viability in storage is the major factor limiting the practical shelf life of blood products. Thus, optimizing conditions for maintenance of red blood cell ("RBC") viability is a central objective in the design of protocols for processing whole blood or concentrated RBCs for storage. For approval under current United States Food and Drug Administration regulations, at least 75% of RBCs transfused after processing and storage according to such a protocol must be viable, i.e. remain in the recipient's circulation system at least 24 hours post-transfusion.

Processing and storage of collected whole blood includes introducing additives at the point of collection and, in some protocols, also after separation into components. Citrate, phosphate, adenine, sodium chloride, and sugar or sugar alcohols are the most common ingredients of the additive solutions. Citrate, typically present as citric acid, as sodium citrate or as a combination thereof, inhibits coagulation. A citrate concentration of at least 5 to 7 mM is desirable for anticoagulation in the expressed plasma. Phosphate, usually sodium phosphate, and adenine help maintain high levels of erythrocytic adenosine triphosphate ("ATP") which is depleted during storage. ATP levels have been found to correlate with RBC viability. Sugars such as dextrose provide fuel for RBC metabolism. Approved treatment protocols typically leave 25 to 30 mg of adenine in the RBC concentrate, with up to 22 mM of citrate ion in the fluid component.

Early approaches to blood processing were oriented to the storage of whole blood. The blood was collected into a solution providing anticoagulant and also nutrients for maintaining the red blood cells during storage. Both acid citrate dextrose ("ACD") and citrate phosphate dextrose ("CPD") solutions have been used for this purpose. Collection with CPD allows 21-day storage of whole blood and was widely used. The development of the derivative composition CPDA-1 was motivated by a demand for longer shelf life. It incorporated the three elements of CPD in the same ratios relative to one another as in CPD but at 125% of their CPD levels; in addition, CPDA-1 also includes adenine. RBCs concentrated from whole blood collected into CPDA-1 meet FDA regulations after 35 days of storage at 1 to 6° C. The CPDA-1 formulation was further optimized expressly for enhancing the shelf life of RBCs concentrated from the processed whole blood. The resulting formulation, known as CPDA-2,contains about 1.4 times the levels of citrate, phosphate, and dextrose, and 2.0 times the amount of adenine found in CPDA-1. Although it was not licensed, CPDA-2 extended the shelf life of RBCs concentrated from stored whole blood to 42 days in conformity with FDA regulations.

Since the mid-1970's, the increasing emphasis on the use of blood components in medical therapy has shifted the emphasis from whole blood storage to the preservation of separated components. This approach eliminates the necessity of providing for the needs of every component at collection, which can expose a component to an additive or a concentration potentially harmful to it; instead, treatments can be tailored to optimize the shelf life and functionality of individual blood components. Thus, the established protocols typically involve first drawing blood into a container containing an additive solution formulated primarily for anticoagulation, then, after centrifugation, expressing the platelet-rich plasma. The remaining concentrated RBCs are, optionally, treated by introducing a second additive solution containing nutrients for maintenance of energy metabolism, or other additives for stabilizing the RBC membrane, such as mannitol and sucrose. Typically, the anticoagulant solution used is CPD or CP2D. A wide variety of RBC-specific additive solutions, typically containing some subset of the constituents already mentioned, are known in the art. Such two-solution protocols are known in the art which produce concentrates having 75% of the RBCs viable at 24 hours post transfusion after 42 days of cold storage.

When nutrients are added directly to the concentrated RBCs rather than to the whole blood, their levels in the concentrate are more easily controlled. The introduction of additive solution to the RBCs after separation is also desirable from a rheological standpoint. The increasing demand for plasma had resulted in the preparation of red cell concentrates with very high hematocrits and correspondingly high viscosities. RBCs concentrated to a hematocrit greater than about 65% infuse more slowly than desired. In some clinical situations, electrolyte or colloid solutions have been added at the time of transfusion to achieve a required flow rate. The constituents of these solutions may be incompatible with the needs of the patient receiving the transfusion. Adding preservative solution to the RBCs before storing offers an opportunity to adjust the flow properties of the concentrate, so that practically all plasma may be extracted from collected whole blood for further processing without affecting the physical properties of the RBC concentrate.

The advantages of two-solution protocols are purchased at the higher manufacturing costs of producing distinct anticoagulant and preservative solutions compared to producing one additive solution, functioning as both anticoagulant and preservative solutions, as is added to whole blood before storage. A process using a single multipurpose additive-solution composition for both anticoagulation and preservative functions would minimize that disadvantage. The prospect of collecting RBCs by pheresis techniques has made such a multipurpose solution even more attractive. The additive solution, serving as anticoagulant, could be introduced into the conduit conveying the blood from the donor to a separator, such as a centrifuge bowl. After the plasma has been removed for return to the donor, more of the same solution, now serving to nourish the cells and adjust the hematocrit, could be added from the same source to an RBC storage unit or to an RBC concentrate in the bowl.

However, no appropriate multipurpose additive-solution composition, which accomplishes the unrelated goals of anticoagulation and maintenance of RBCs for extended periods (e.g., the 42 days of storage achieved with two-solution techniques or with the wholeblood/CPDA-2 approach), has yet been identified. Consider, for example, using CPDA-1 as both anticoagulant and preservative. A 30-ml addition of CPDA-1 to 450 ml of whole blood collected in a pheresis apparatus (a 1:15 solution-to-blood ratio) would result in a satisfactory anticoagulant level—about 11.0 millimolar ("mM")—in the expressed plasma. The remaining RBC concentrate would contain about 180 ml of RBCs and 45 ml of plasma, corresponding to a hematocrit of about 80%. A 30-ml second increment of CPDA-1 added to the RBC concentrate for nourishment during storage would provide about 3.6 millimoles of citrate to the final concentrate with about 9 mg total adenine, an insufficient level of adenine to support 42 days of storage. The hematocrit of the RBC concentrate after such an addition would be undesirably high, greater than 70%. To reduce the hematocrit to 63%, a 60-ml second increment would be required. A 60-ml second increment of CPDA-1 would produce a concentrate having total adenine content at an acceptable level of about 17 mg, but the ultimate citrate content would be about 6.7 millimoles, much higher than the levels found using currently licensed products. Such a high citrate level may be harmful to the patient receiving the RBCs and may also have a deleterious effect on RBCs during storage.

Although other RBC diluents can be used with CPDA-1 to bring the citrate to a clinically acceptable level, the resulting concentrates do not satisfy the 42-day storage requirement. A statistical analysis of data collected by the American Red Cross of the Mid-Atlantic Region indicates an 80% probability of 75% RBC survival 24 hours post-transfusion for a concentrate in which the mean ATP levels are greater than 2.7 µmoles/g hemoglobin, and with less than 0.5% of the RBCs hemoglobin released extracellularly (% haemolysis) (see, e.g., Heaton W. A. L., Evaluation of posttransfusion recovery and survival of transfused red cells, TRANSFUSION MEDICINE REVIEWS, Vol. VI, No. 3, 1992). The suitability of normal saline solution (i.e., about 0.9% aqueous sodium chloride) as a diluent for the second increment of CPDA-1 added to RBC concentrates has been evaluated according to these criteria. ATP and haemolysis levels were measured for units receiving a total of 100 ml solution containing CPDA-1 plus saline after being initally collected into 30 ml of CPDA-1 and then concentrated to about-80% hematocrit.

The second increment compositions studied were 30 ml CPDA-1/70 ml saline, 60 ml CPDA-1/40 ml saline and 80 ml CPDA-1/20 ml saline. RBC concentrates prepared according to this procedure did not conform to the in vitro predictors of clinical success as well as did the concentrates made by known two-solution protocols. Although the concentrates had satisfactory haemolysis levels on day 42, they did not maintain the benchmark ATP level during the required storage period, the concentrations having fallen from about 4 µmoles/g Hb on the day of collection to less than 2.7 µmoles/g Hb by day 35.

Neither do these results suggest alternate second-increment or additive-solution compositions likely to extend the concentrate shelf life. Within the compositional range studied, neither the ATP nor haemolysis levels clearly correlate with the concentration of the additives in the second increment. The irregularity of these data underscores the impracticality of obtaining the desired RBC-concentrate attributes simply by modifying the additive-solution composition in an intuitive manner—that is by adding higher concentrations of materials known to have a positive effect. For example, increasing adenine levels based on an observation of lengthening shelf life with adenine content did not result in improved ATP and hemolysis levels.

DESCRIPTION OF THE INVENTION

Objects of the Invention

An object of the present invention is, accordingly, to provide a protocol for producing a red blood cell concentrate with 75% viable RBCs and hemolysis <1% after 42 days of storage at 1° to 6° C.

Another object of the invention is to provide a protocol for producing a red blood cell concentrate having a hematocrit compatible with a practical transfusion rate.

Still another object of the invention is to produce a red blood cell concentrate having benign citrate levels.

Another object of the invention is to provide a single additive-solution composition suitable for both anticoagulation and preservative functions in a two-solution red blood cell concentration protocol.

Another object of the invention is a pheresis apparatus for concentrating red blood cells that incorporates only one additive solution source.

Brief Summary of the Invention

The present invention provides a method of treating blood that uses a single additivesolution composition for both the initial anticoagulation of collected whole blood and the longterm preservation of concentrated red blood cells. The additive formulation of the invention contains citrate at a reduced concentration with respect to its concentration in CPDA-1. A representative formulation, hereinafter referred to as 0.5CPDA-1, contains adenine, phosphate, and dextrose at the concentrations at which they are found in CPDA-1 with one-half the total citrate content of CPDA-1. However, the invention is not limited to this composition, but encompasses the use of all reduced-citrate solutions that can function as both anticoagulant and preservative and effect the RBC longevity required for extended storage of the RBC concentrate. The additive solutions of the invention may be characterized in terms of either absolute citrate concentration or the ratio of citrate to other additive constituents. Solutions having total citrate concentrations less than 80 mM, preferably less than 60 mM, e.g. between 45 and 60 mM, are suitable. Adenine concentrations between 1.7 and 2.3 mM are compatible with these citrate concentrations. The invention also includes compositions containing citrate and adenine at a molar ratio less than 40, especially less than 30.

The beneficial effect of the reduced citrate concentration compared to known RBC preservative solutions, which allows the multipurpose use of a single additive-solution composition according to the invention, is surprising in light of the studies of CPDA-1 already mentioned. No correlation of levels of ATP or haemolysis with citrate levels in the RBC concentrate was observed for final concentrations ranging from 25 mM, which falls within the range achieved by the embodiment of the invention detailed above, to greater than 60 mM.

The reduced-citrate additive solution of the invention functions as an anticoagulant when added to whole blood collected from a donor, for example by introduction into a conduit conveying the whole blood from the donor to a separator. After the anticoagulated plasma has been expressed, the same additive solution is introduced into the concentrated red blood cells to provide nutrients during storage. The possibility of using a single additive solution is especially advantageous for pheresis collection of red blood cells; it allows simplification of the processing apparatus by the elimination of a second solution source.

A preferred embodiment of the invention provides 0.5CPDA-1 to whole blood at a 1:7 volume ratio during collection. After centrifugation has reduced about 450 ml of whole blood to a roughly 225-ml RBC concentrate of about 80% hematocrit, a second increment of 0.5C-PDA-1 is added. Excellent results are obtained with second increments of 60 to 80 ml 0.5C-PDA-1.

This procedure effects a citrate concentration of about 10 mM in the expressed plasma and a total citrate content of about 3.6 to 4.7 millimoles in the final RBC concentrate, only moderately higher than levels used in RBC products prepared using licensed solutions. The final adenine level ranges from about 18 to 25 mg. At about 59% to 63%, the resulting concentrate hematocrit, allows for easy transfusion of the cells.

In another embodiment, a second increment of 60 to 80 ml 0.5 CPDA-1 and supplemental normal saline brings the total second increment volume to 100 ml. RBCs processed according to this protocol have shown mean ATP levels greater than the benchmark level of 2.7 μ moles/g Hb after 42 days of cold storage and haemolysis lower than 0.5% even after 49 days of cold storage, indicating good probability of 75% RBC survival post-transfusion. Concentrates prepared using a single additive-solution composition with a second increment of 70 ml 0.5CPDA-1 and 30 ml normal saline perform at least as well as currently licensed techniques. For example, such concentrates have shown mean ATP and haemolysis values within experimental error of day-35 and day-42 levels reported for RBCs concentrated from anticoagulated whole blood and then receiving AS-3 preservative solution, commercially available from Med Sep Corporation.

BRIEF DESCRIPTION OF THE DRAWINGS

The foregoing discussion will be understood more readily from the following detailed description of the invention, when taken in conjunction with the accompanying drawings, in which:

It will appreciated that, for purposes of illustration, FIGS. 5 and 6 are not necessarily drawn to scale.

DETAILED DESCRIPTION OF THE INVENTION

In a preferred embodiment of the invention, the additive solutions of the invention include phosphate, dextrose, and adenine in the following ratios to citrates based on molar concentrations:

| phosphate | 0.28–0.48 |
| dextrose | 2.5–4.2 |
| adenine | 0.026–0.044 |

The performance of the reduced-citrate additive solutions of the preferred embodiment can be demonstrated with reference to a representative solution 0.5C-PDA-1, which can be prepared by adding distilled water to the following to make 500 ml:

| citric acid | 0.745 g |
| sodium citrate dihydrate | 6.585 g |
| monobasic sodium phosphate | 1.11 g |
| dextrose | 15.95 g |
| adenine | 0.135 g |

Equivalent formulations of 0.5C-PDA-1 having different citrate components or citrate component concentrations are possible, as long as the total citrate concentration is equal to about 52 mM, half of the citrate concentration of CPDA-1.

The effectiveness of using a single additive-solution composition of reduced citrate concentration for red blood cell concentration is demonstrated by the data presented below. Each of three 450-ml units of whole blood was collected into a bag containing 64 ml of 0.5C-PDA-1 (1 part of additive solution for 7 parts of blood). The three concentrates were mixed and the pooled product redivided into three quantities of approximately 514 ml. Each quantity was centrifuged to remove about 276 ml of fluid, including additive solution and plasma, bringing the resulting 238 ml of RBC concentrate to a hematocrit of about 80%. The citrate levels in the separated plasma were about 10.4 mM. Each of the three concentrates received a second increment, a total volume of 100 ml, containing 0.5C-PDA-1 and normal saline composed according to one of three 0.5C-PDA-1/saline ratios: 60/40, 70/30 or 80/20. The concentrates were stored at 1° to 6° C. The mean ATP and haemolysis levels of each concentrate were measured at 1, 35, 42, and 49 days of storage. This procedure was completed for five sets of donors.

The above-mentioned study of the storage performance of RBC concentrates treated by CPDA-1 /saline additions was executed according to a parallel procedure. Units of 450 ml of whole blood collected into 30 ml of CPDA-1 were mixed and the pooled product redivided into 480-ml quantities. After centrifugation to a hematocrit of about 80%, a total of 100 ml CPDA-1 plus normal saline, in a ratio of 30/70, 60/40 or 80/20, was added to each of the concentrates.

Figure 1:
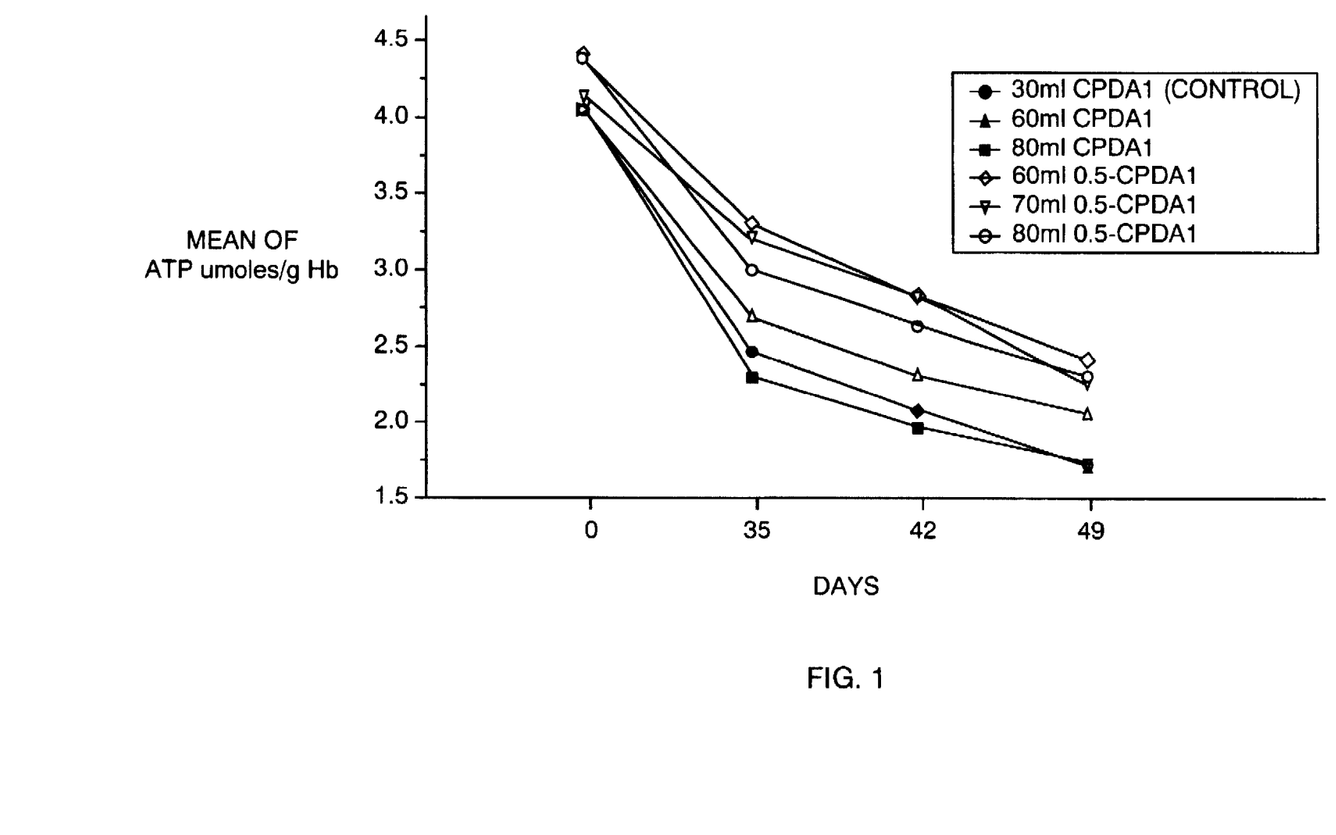
FIG. 1 graphically depicts mean ATP levels in red blood cell concentrates prepared using single additive-solution compositions.
Figure 2:
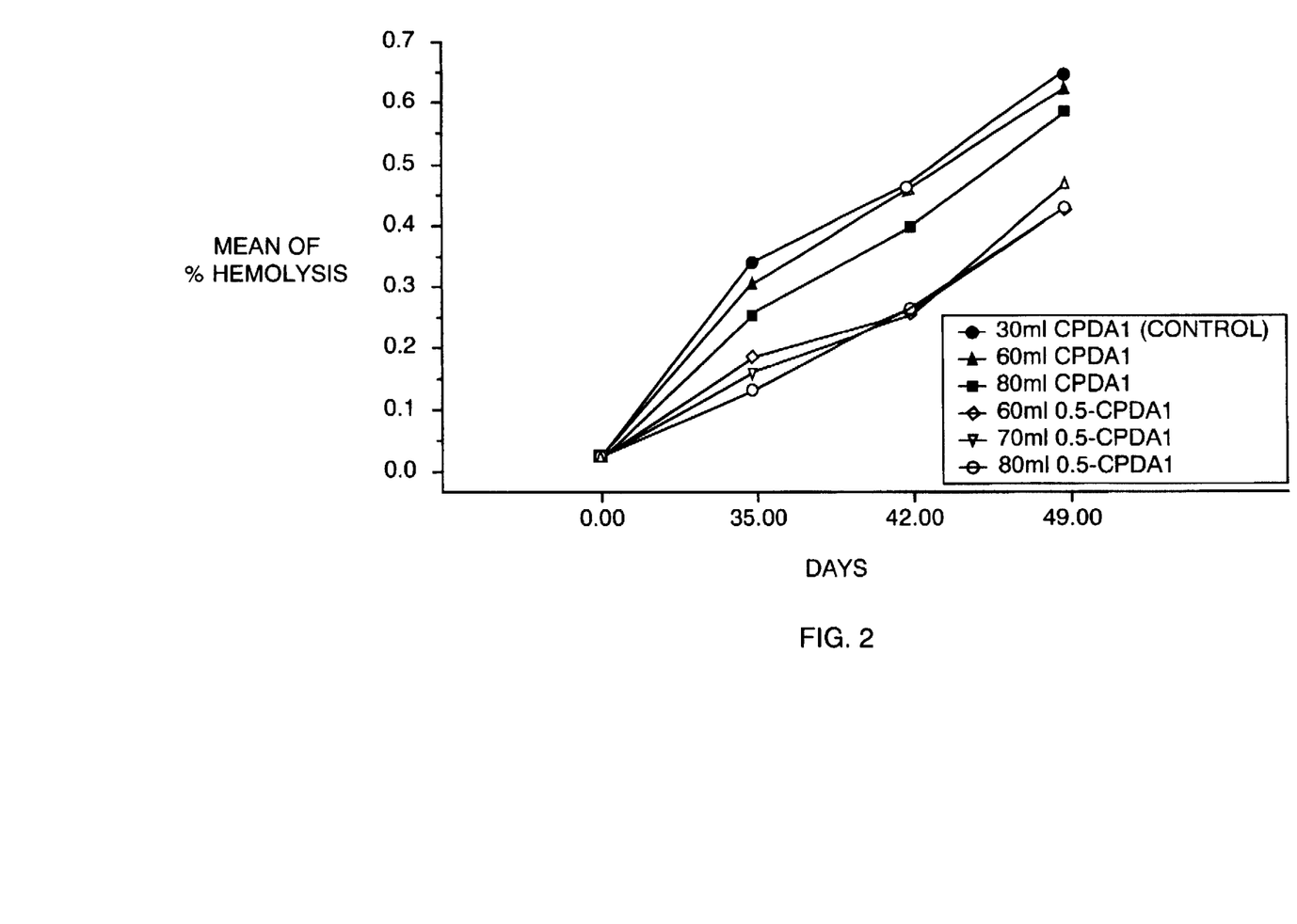
FIG. 2 graphically depicts haemolysis levels in red blood cell concentrates prepared using single additive-solution compositions.
Figure 3:
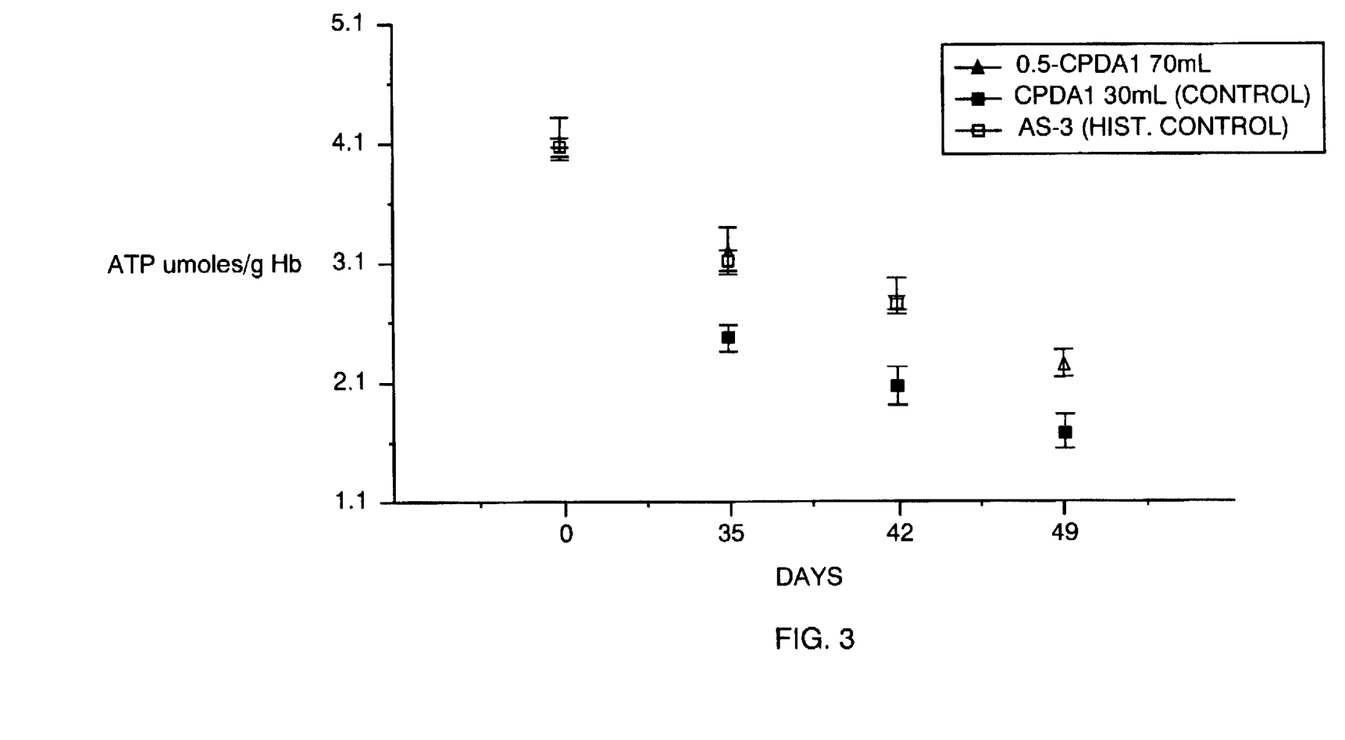
FIG. 3 graphically depicts the mean ATP levels in red blood cell concentrates prepared using single additive-solution compositions and an anticoagulant/AS-3 preservative protocol.
Figure 4:
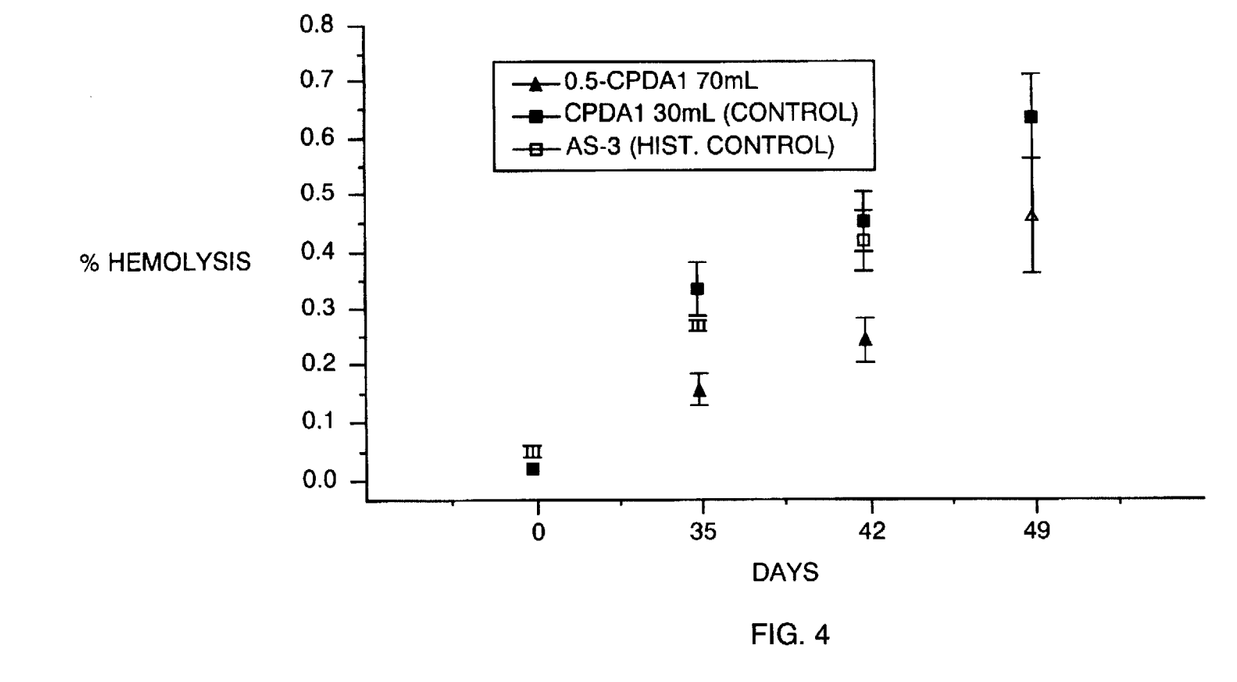
FIG. 4 graphically depicts the haemolysis levels in red blood cell concentrates prepared using single additive-solution compositions and an anticoagulant/AS-3 preservative protocol.

FIGS. 1 and 2 show the behavior of the measured values over time for the two different single additive-solution compositions. Both the mean ATP and haemolysis values shown indicate the benefit of the reduced citrate concentration in the additive solution for the protocols of the invention. FIGS. 3 and 4 compare the values measured for a second increment of 70 ml 0.5C-PDA-1 and 30 ml normal saline with those measured for a second increment of 30 ml CPDA-1 and 70 ml normal saline and also with values reported for RBCs concentrated from anticoagulated whole blood and then receiving AS-3 preservative solution. (AS-3 contains citrate, phosphate, dextrose and adenine, with concentration profiles similar to CPDA-1, in a saline vehicle.) The indicators for the concentrate produced by the procedure using the 0.5CPDA-1 solution of the invention are comparable to the reported AS-3 values and clearly more favorable than those for the concentrates produced using CPDA-1. The use of a single additive-solution composition having reduced citrate appears to protect RBC longevity as effectively as the anticoagulant/AS-3 approach without the need for a distinct additive-solution compositions for each of the anticoagulant and nutrient functions.

Figure 5:
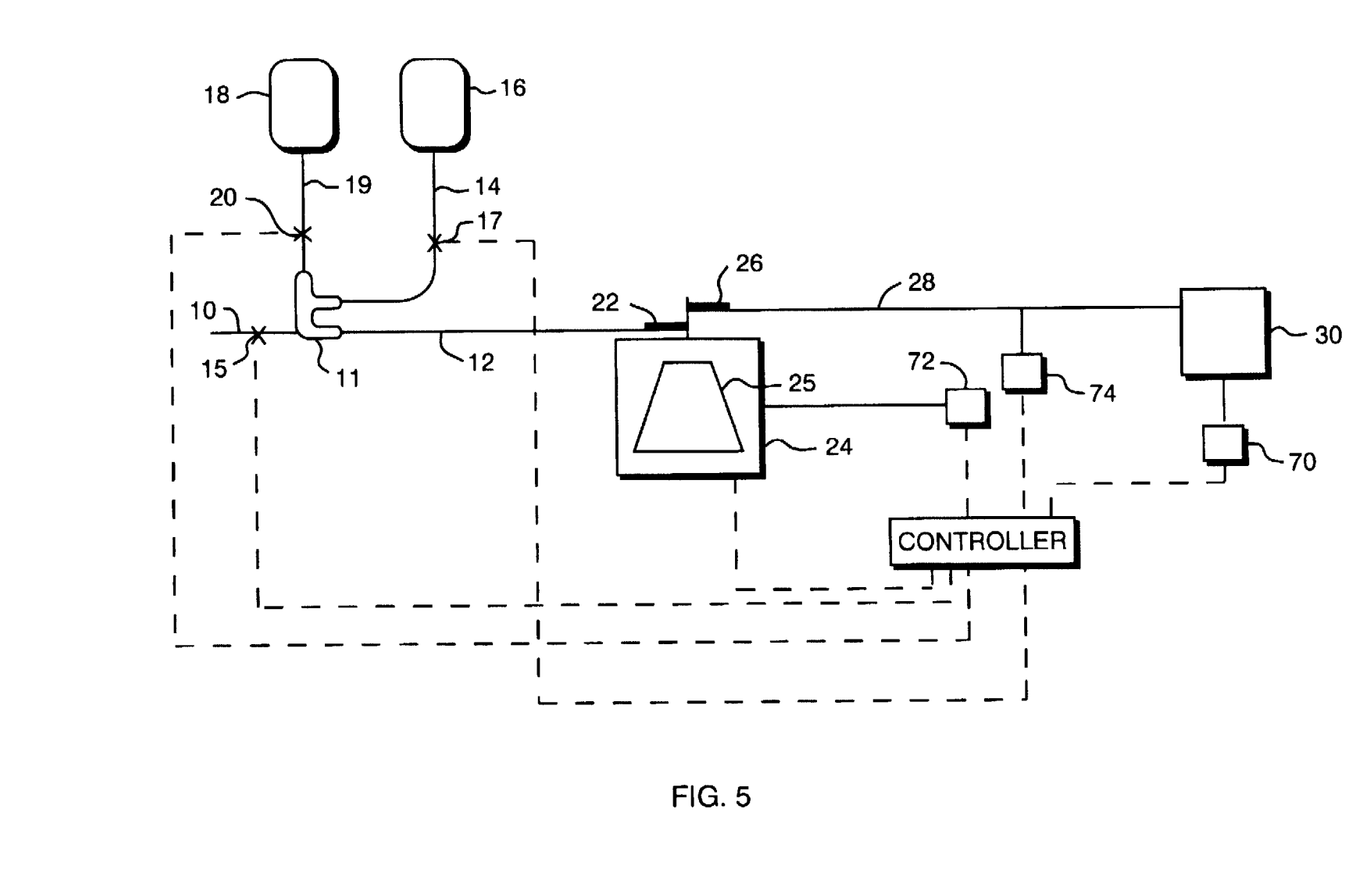
FIG. 5 schematically illustrates a blood-processing apparatus compatible with the method of the invention.

FIG. 5 shows a blood-processing system with which the reduced-citrate additive solutions of the present invention may be used. A tube 10 collects blood from a donor. A coupling 11 joins tube 10 to a collection line 12 and an additive solution line 14. A valve 15 allows isolation of the donor from the rest of the system; this valve may be, for example, a ratchet clamp. An additive solution source 16, containing the additive solution of the invention, communicates fluidly with coupling 11 through the additive solution line 14. The additive solution line 14 has a valve 17, such as a roller clamp, by which the flow rate of additive solution into the collection line is regulated. Optionally, the system may additionally include a diluent source 18, containing a diluent such as normal saline solution, communicating fluidly with coupling 11 through a wash solution line 19 having a valve 20.

Collection line 12 connects to the inlet port 22 of a centrifuge bowl 25, which is itself part of a centrifuge apparatus 24 that comprises the bowl 25 and means for rotating it (not shown). The outlet port 26 of centrifuge bowl 25 is connected by an effluent line 28 to a plasma collection bag 30. The centrifuge bowl 25 shown in FIG. 6 comprises a nonrotatable assembly joined to a rotatable bowl body by a rotary seal. The nonrotatable assembly comprises the inlet port 22, an inlet tube 40 extending into the bowl body from the inlet port 22, and a collection chamber 41 communicating with the output port 26. The bowl body comprises an outer wall 44 and an coaxial inner wall 46 forming a separation chamber 48 between them.

Figure 6:
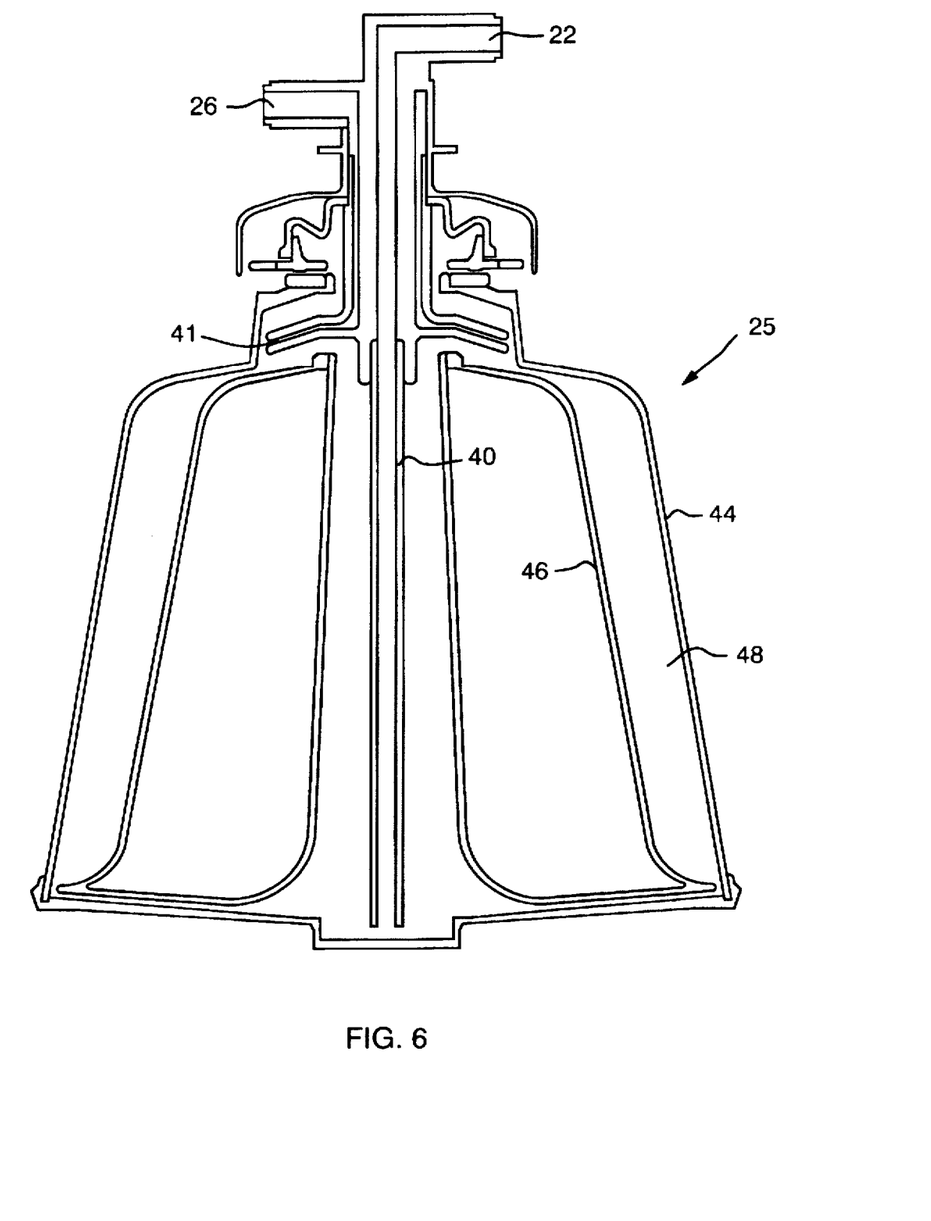
FIG. 6 schematically illustrates a centrifuge bowl.

In operation, blood is conveyed from the donor through the tube 10 and coupling 11 into the collection line 12. The valve 14 operates to allow solution from the additive solution source 16 to mix with the collected whole blood at coupling 11. Preferably, the valve 14 is operated to provide a specific overall blood-to-additive solution mixing ratio, such as, for example, approximately 7 to 1. The citrate ion provided by this first increment of additive solution inhibits coagulation. The diluted blood enters input port 22 and passes into the separation chamber 48 of centrifuge bowl 25. When the desired volume of whole blood has passed through the collection line, closing the valve 15 prevents further blood from entering the centrifuge bowl 25. Valve 20 may also be optionally operated to allow diluent to mix with the blood during collection or after collection has been completed.

Rotation of the bowl concentrates the red blood cells against the outer wall 44. With continued influx of blood, the supernatant, comprising lighter blood components and additive solution and/or diluent, forms concentric layers that approach the inner wall 46 until they reach collection chamber 41 and exit out the outlet port 26. The effluent line 28 carries the exited supernatant to the plasma-collection bag 30. When the desired concentration of the red blood cells has been obtained in the bowl 25, bowl rotation is stopped. The valve 14 is then operated to introduce a second increment of additive solution into the bowl 25. Optionally, valve 20 is also operated at this time to introduce diluent from the diluent source 18 in order to reduce the hematocrit of the RBC concentrate.

Several variations of the foregoing system are consistent with the scope of the present invention. The system may provide for expressed plasma to be returned directly to the donor rather than collected in the plasma collection bag 30. The system may optionally include peristaltic pumps in the collection, additive solution, or diluent lines to encourage fluid movement through the system. Or, vacuum could play this role. Sensors may be incorporated to indicate how much blood has entered the system, such as a gravimetric sensor 70 to read the weight of the plasma-collection bag 30 or an optical sensor 72 or 74 at the centrifuge bowl 25 or in the effluent line 28 to indicate when the red blood cells have attained a desired concentration. Operation of the centrifuge 24 or of any of the valves 15, 17 or 20 may be effected by a programmable controller 90, which receives input from any of the aforementioned sensors and operates in accordance with predetermined criteria. For example, the controller might operate these components to terminate collection once a sufficient volume of blood has been collected. These control functions can be implemented without undue experimentation by those skilled in the art using conventional microprocessor circuitry and programming techniques.

It will therefore be seen that the foregoing represents a highly advantageous approach to blood processing, especially for preparation of blood components for storage. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of processing blood from a source, the method comprising the following steps:
   a. removing whole blood from a donor;
   b. adding a first quantity of an aqueous solution thereto, the solution having a total citrate concentration greater than zero and less than 80 mM;
   c. removing plasma from the blood so as to produce a concentrate containing red blood cells; and
   d. adding a second quantity of said aqueous solution to the concentrate.

2. The method of claim 1 wherein the aqueous solution further comprises adenine.

3. The method of claim 2 wherein the solution comprises adenine at a concentration between 1.7 and 2.3 mM.

4. The method of claim 2 wherein the solution has a total citrate/adenine molar ratio greater than zero and less than 40.

5. The method of claim 1 wherein the aqueous solution further comprises dextrose.

6. The method of claim 1 wherein the aqueous solution further comprises phosphate.

7. The method of claim 1 wherein the total citrate concentration is less than 60 mM.

8. The method of claim 7 wherein the solution comprises adenine at a concentration between 1.7 and 2.3 mM.

9. The method of claim 1 wherein the total citrate concentration is between 45 and 60 mM.

10. The method of claim 9 wherein the solution comprises adenine at concentration between 1.7 and 2.3 mM.

11. The method of claim 1 wherein the solution has a total citrate/adenine molar ratio less than 30.

12. The method of claim 1 wherein the solution contains one molar part citrate and further comprises, by molar part,
   phosphate 0.28–0.48
   dextrose 2.5–4.2
   adenine 0.026–0.044.

13. The method of claim 1 wherein the whole blood is present at an initial volume and the first quantity is about 1/7 of the initial volume.

14. The method of claim 1 wherein the addition of the first quantity results in a citrate concentration in the removed plasma equal to at least 6 mM.

15. The method of claim 1 wherein the concentrate has an initial concentrate volume before adding the second quantity and the second quantity is about 25% of the initial concentrate volume.

16. The method of claim 1 wherein the concentrate has a hematocrit less greater than zero and less than 65% after addition of the second quantity.

17. The method of claim 1 further comprising the step of adding an amount of normal saline solution to the concentrate.

18. The method of claim 17 wherein the concentrate has a hematocrit greater than zero and less than 65% after adding the amount of normal saline.

19. The method of claim 17 wherein the amount of normal saline solution is from one-fourth to two-thirds of the second quantity.

20. The method of claim 1 wherein the concentrate has a liquid component and the citrate concentration in the liquid component is less than 60 mM after adding the second quantity.

21. A method of processing blood from a source, the method comprising the following steps:
   a. removing whole blood from a donor;
   b. adding thereto a first quantity of an aqueous solution the solution comprising citrate and adenine at a citrate/adenine molar ratio less than 40;
   c. removing plasma from the blood so as to produce a concentrate containing red blood cells; and
   d. adding a second quantity of said aqueous solution to the concentrate.

22. The method of claim 21, wherein the solution contains one molar part citrate and further comprises by molar part, phosphate 0.28–0.48 dextrose 2.5–4.2 adenine 0.026–0.044

23. The method of claim 21 wherein the solution contains, by molarity, citrate 48–52 mM phosphate 17–20 mM dextrose 160–190 mM adenine 1.8–2.2 mM.

24. The method of claim 23 wherein the whole blood is present at an initial volume and the first quantity is about 1/7 of the initial volume.

25. The method of claim 23 wherein the concentrate has an initial concentrate volume before adding the second quantity and the second quantity is about 25% of the initial concentrate volume.

26. The method of claim 23 further comprising the step of adding an amount of normal saline solution to the concentrate.

27. The method of claim 26 wherein the amount of normal saline solution is from one-fourth to two-thirds of second quantity.

28. The method of claim 21 wherein the total citrate/adenine molar ratio is less than 30.

* * * * *